United States Patent [19]
Lenaghan

[11] 3,941,132
[45] Mar. 2, 1976

[54] INTERCONNECTED SURGICAL SPONGES
[76] Inventor: Arlene Lenaghan, 486 Wishbone Drive, Bloomfield Hills, Mich. 48013
[22] Filed: Nov. 27, 1974
[21] Appl. No.: 527,733

[52] U.S. Cl. .............................................. 128/296
[51] Int. Cl.² ......................................... A61F 13/00
[58] Field of Search ............. 128/296, 269, 155–157

[56] References Cited
UNITED STATES PATENTS
3,095,877   7/1963   Rowan ............................ 128/296 X
3,630,202  12/1971   Small ................................. 128/296

Primary Examiner—Lawrence W. Trapp
Attorney, Agent, or Firm—Cullen, Settle, Sloman & Cantor

[57] ABSTRACT

Surgical sponges which are interconnected by a linear connector and which may be used in surgical procedures without disconnecting the sponges. The sponges are serially retained on the connector in spaced relation and may be easily extended by tensioning the connector. The connector includes gathered or accumulated portions which are removably retained to the sponges for extension during the operating procedures.

14 Claims, 5 Drawing Figures

INTERCONNECTED SURGICAL SPONGES

FIELD OF THE INVENTION

This invention relates to surgical sponges which are presently utilized to absorb body fluids in surgery or operating procedures.

Surgical sponges are gauze pads which may also include a thin creped paper lining to improve their absorbency. Surgical sponges are presently sold in various sizes and are generally received in sterilized packages in quantities of two to 20 sponges, although surgical procedures generally require 10 or more sponges.

During an operation, for example, the sponges are placed by the surgeons directly in the incision to absorb blood and other body fluids. The sponges are removed by the surgeons and their assistants during the operation and immediately prior to closure. Further, surgical sponges may be contaminated prior to insertion and surgical sponges are often discarded on the operating floor and in other places. Sponges may not however be left in the incision because they are a foreign body and their presence may result in infections and other problems. There is an important need therefore for a procedure which will assure that no surgical sponges remain in the patient following surgery. This is presently accomplished by two or more surgical sponge counters whose responsibility is to count all sponges prior to use and to recount the sponges following use. A simple tag system cannot be utilized because several packages of sponges may be utilized during a single operation. Further, weighing techniques have not been successful because surgical sponges generally absorb many times their own weight in blood and body fluids, the amount not being predictable or measurable. The interconnected surgical sponges of the present invention minimize or substantially eliminate the possibility of leaving a sponge in a patient following surgery and the interconnected surgical sponges substantially limit the task of counting the surgical sponges before and after surgery. Presently, several hours may be spent following surgery in an attempt to locate a missing sponge to assure that the sponge has not been left in the patient. The number of sponges actually left in patients has further exacerbated the rising cost of malpractice insurance and suits.

SUMMARY OF THE INVENTION

The surgical sponges in the present invention are interconnected by a flexible linear element, such as a string, ribbon or wire. The surgical sponges are located along the length of the linear element and preferably at least one of the sponges are affixed to the element. The length of the element must be greater than the composite length of the sponges and the element includes gathered portions also greater in length than the length of the sponges. The gathered length is then removably retained to each of the sponges, such that the gathered portion is extensible between the adjacent sponges when tensioned for selectively and successively increasing the length between the adjacent sponges. In the preferred embodiment, the linear element is affixed to one end of each of the sponges and may be disposed within the sponges for extension between the sponges, when tensioned. In the disclosed embodiment, the linear element is folded or looped within the sponges and the sponges each include an opening through which the linear element is extended. The linear element may also be absorbant, such as a sterilized cotton tape or ribbon which may be folded flat within the sponge for easy extension through the sponge opening. Alternatively, the linear element may be a wire, such as a plastic coated wire, which would not be accidentally cut by the surgeon during an operation.

The interconnected surgical sponges of this invention are disposable and may be pre-packaged in sterilized, pre-counted packages available for immediate use by the surgeon. The surgical sponges may be individually taken from the package, letting out whatever length of connector is required to place the sponge at the operating site. In the preferred embodiment, the sponges are interconnected by a substantial length of gathered connector, such as 6 feet. When it is desired to remove and dispose of any surgical sponge in the series, the sponge may be discarded in the usual manner because of the substantial length of the gathered portion of the linear connector. In the preferred procedure, the sponges remain interconnected, such that the sponges may be easily checked and counted. In the event that the connector is accidentally or purposely cut during the surgical procedure, this fact may be immediately taken into account and the remaining sponges will still be interconnected substantially reducing the chances of leaving a sponge in the patient. The connector itself will trail from the incision, giving notice of the presence of the sponge and making the sponge easy to identify and locate.

The interconnected surgical sponges of this invention therefore reduce the chances of accidentially leaving a sponge in the patient following surgery and further reduce the time required for checking and counting the surgical sponges used. Further, the interconnected surgical sponges of this invention are particularly adaptable to the present procedures for checking the loss of blood during an operation. In this procedure, all of the surgical sponges used in the operation may be weighed following surgery, providing a check of the amount of blood lost. Where the sponges are interconnected, as in the present invention, the location of all of the sponges utilized in the operation is greatly simplified. Other advantages and meritorious features of the present invention will be more fully understood from the following description of the preferred embodiments, procedures, the appended claims and the drawings, a brief description of which follows.

DESCRIPTION OF THE PREFERRED EMBODIMENTS

Figure 1:
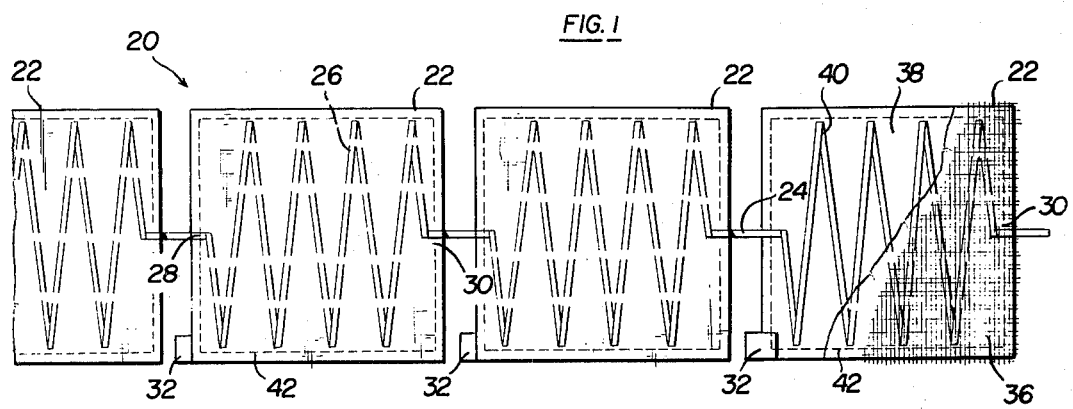
FIG. 1 is a top elevation of a plurality of surgical sponges interconnected as taught by the present invention.
Figure 2:
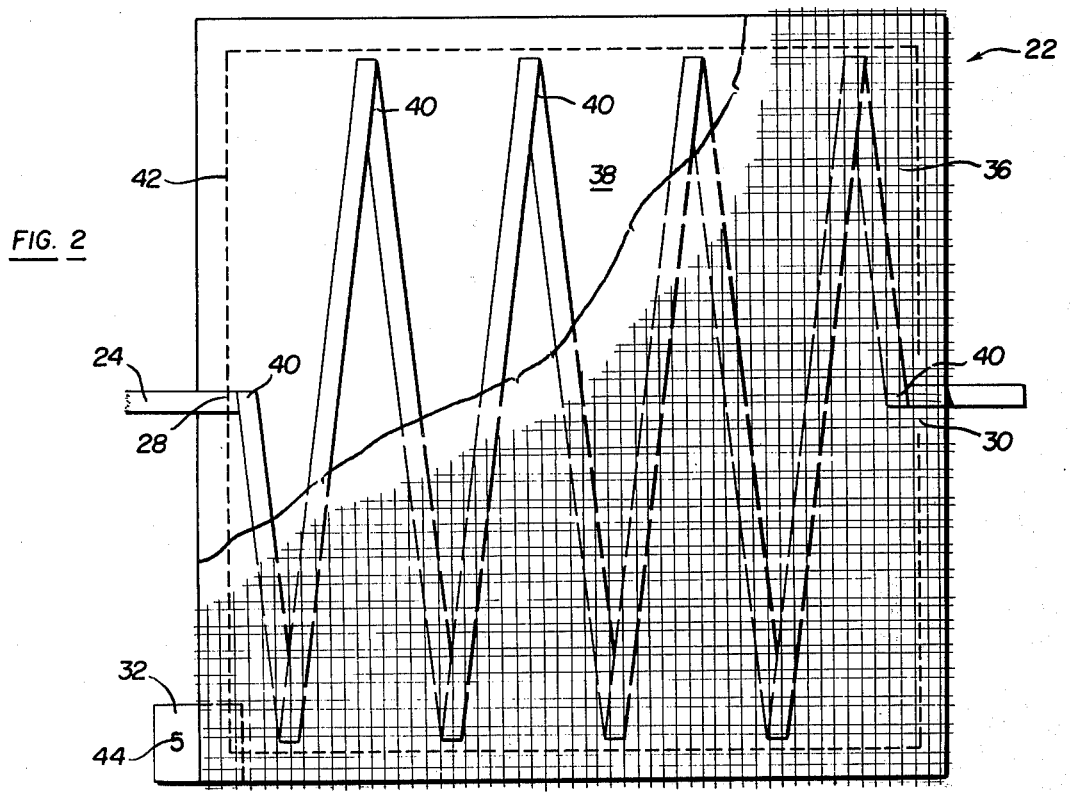
FIG. 2 is a partial top elevation of one of the sponges shown in FIG. 1.

The interconnected surgical sponges 20 shown in FIGS. 1 and 2 include a plurality of conventional surgical sponges 22 interconnected by linear connector 24. As shown, the linear connector 24 includes a plurality of gathered or accumulated portions 26 which are disposed within the surgical sponges and the sponges are fixed at 28 on the connector. In the disclosed embodiment, the sponges each include an open end portion 30 through which the linear connector extends when tensioned and each surgical sponge includes an indicator tab 32 which is secured to the sponge as described below.

The disclosed surgical sponges may be of conventional design including an outer layer of surgical gauze 36 and creped paper liner 38 which improves the absorbency of the gauze. In a conventional surgical sponge, a relatively thin sterile sheet of creped paper is laid over a sheet of surgical gauze and the creped liner is heat sealed or adhesively bonded to the gauze at the peripheral edges. Normally, the longitudinal edges of the gauze are then folded over, the sponge folded and the folded sponge ironed under heat to assure sterilization and uniform size and thickness. As described above, surgical sponges are available in various sizes. For example, conventional sizes for surgical sponges are 4 × 4 inches, 6 × 6 inches, etc. to 10 × 10 inches. The size of the sponges utilized by the surgeon will depend upon the type of operation. For example, operations which cut across the entire abdomen generally utilize 10 × 10 inch sponges. Further, surgical sponges are packaged in various quantities, although quantities of 10 and 20 are generally preferred in surgery.

In the embodiment of the interconnected surgical sponges shown in FIGS. 1 and 2, the linear connector 22 is an absorbent relatively flat ribbon or tape, such as a cotton ribbon, which is folded in a zig-zag pattern having relatively flat folds 40, as best shown in FIG. 2. As described above, the sponge is preferably fixed to the ribbon adjacent one edge, as at 28. In this embodiment, the periphery of the sponge is stitched, such as by a conventional hemming stitch, which retains the ribbon at 28 and further retains the indicator tab 32. In the disclosed embodiment, the indicator tab includes an indicia 5 to identify the location of the particular sponge in the string. The number will notify the surgeon when he is approaching the end of the string, permitting the surgeon to call for another package of surgical sponges. Similarly, the indicator tabs may be colored either to identify the location of the surgical sponge or to differentiate between different packages of sponges. An identification number may also be printed directly upon the surgical sponge. The identification tab may also be utilized in conjunction with a counter system, wherein a counter is disposed with the sponge to make certain that each of the sponges has been removed from the incision.

The extended length of the gathered portion 26 of the linear connector is particularly important to the interconnected surgical sponges of this invention. As described, the gathered or accumulated portion of the linear connector may be easily extended from within the surgical sponge by tensioning the connector. As described, in the preferred embodiment, the sponge is affixed to the connector adjacent one edge, such that the linear connector is extended through the open end 30 of the sponge, thus increasing the distance between adjacent sponges. The extended length of the gathered portion of the connector is preferably at least 50 inches in length and may be 6 feet in length or greater. The length of a surgical sponge is generally between 4 and 10 inches, such that the accumulated length of the connector is substantially greater than the length of the individual sponges. The surgical sponges may thereby be taken from the package, as described above, placed in the incision and even discarded, if necessary, while remaining in the string. The method of use of the sponges will be discussed in regard to FIGS. 4 and 5.

Figure 3:
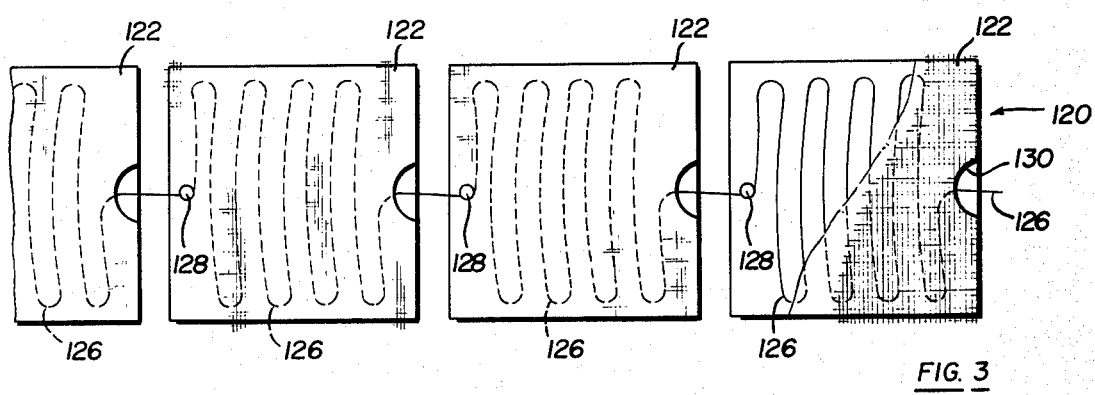
FIG. 3 is another embodiment of the interconnected surgical sponges of this invention.

FIG. 3 discloses another suitable embodiment of the interconnected surgical sponges of this invention and FIG. 3 has been numbered in the same sequences as FIG. 1. As described, the interconnected surgical sponges 120 include a plurality of surgical sponges 122 which are interconnected by a linear connector 124. In this embodiment, the linear connector is a flexible wire, such as conventional surgical wire or plastic coated wire. The embodiment of FIG. 3 has the advantage that the wire will not be accidentally cut during conventional surgical procedures. In this embodiment, the wire is gathered or looped within each of the sponges, defining the gathered portion 126. The surgical sponges are affixed to the wire at 128 by any suitable means, such as a plastic snap fastener or grommet. Further, one layer of the surgical sponge has been cut at 130 to provide an opening for extension of the gathered portions 126 of the connector as described above.

Figure 4:
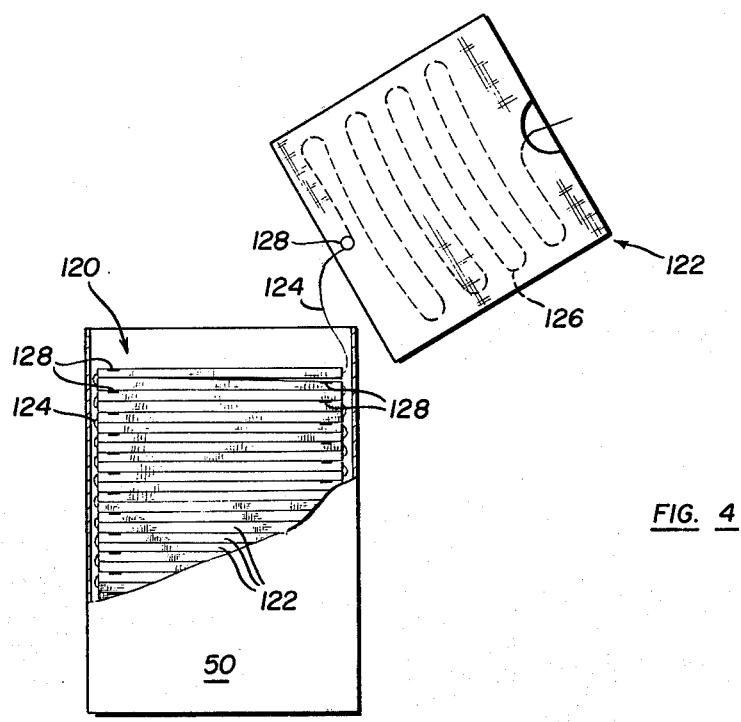
FIG. 4 illustrates the surgical sponges of this invention packaged for use; and, FIG. 5 illustrates how the interconnected surgical sponges of this invention may be used.

FIG. 4 illustrates a package of surgical sponges as received for use. The sponges 122 are packed in face-to-face relation with the linear connector portion extending between the serially interconnected sponges. In the preferred embodiment, approximately one inch of linear connector initially extends between adjacent sponges, permitting packaging as shown. As described, the interconnected surgical sponges 122 of this invention are preferably packaged in sterilized packages or containers 50 in pre-counted quantities. The surgical sponges may be removed from the container simply by lifting one, two or the desired quantity from the package 50. In FIG. 4, one surgical sponge 122 has been removed from package 50 for use. As shown, connector 128 prevents relative movement of the surgical sponges on the connector 124. Tensioning of the connector 124 plays out the linear connector from the next sponge in line, permitting insertion of the surgical sponge in an incision, for example, during surgery. The use of the sponges is best shown in FIG. 5.

Figure 5:
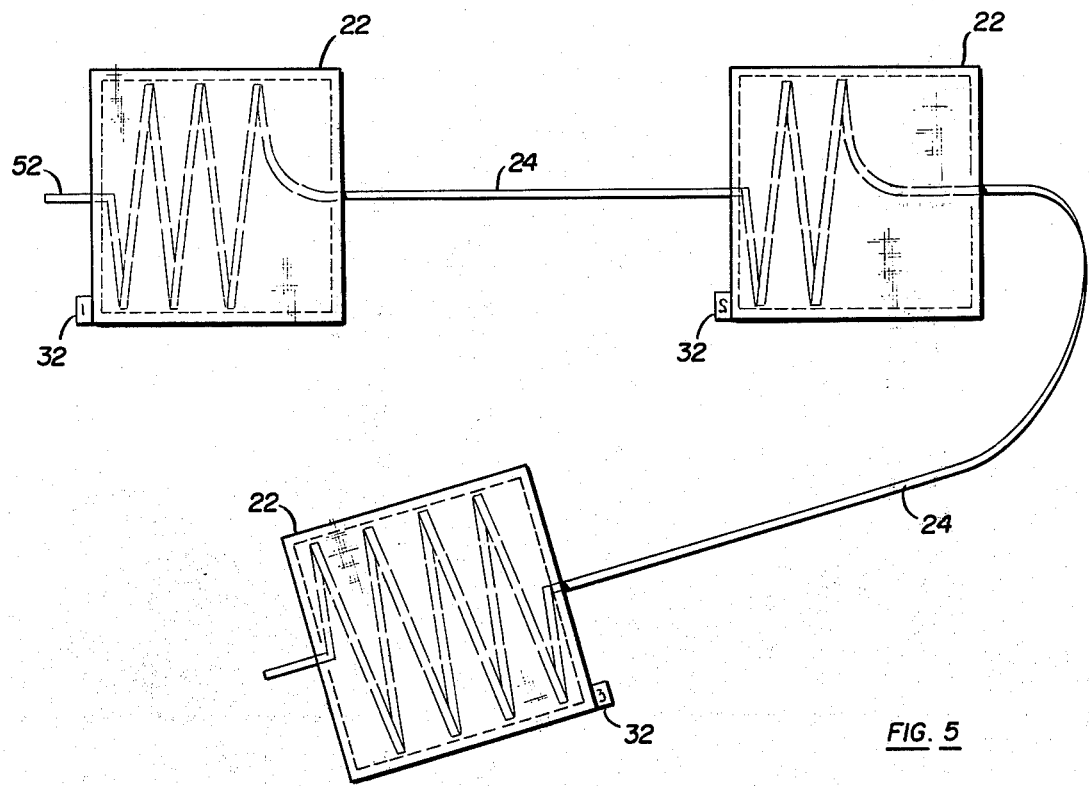

FIG. 5 illustrates the use of the surgical sponges which have been arranged as required by the particular application. For example, the surgical sponges identified as 1 and 2 have been placed generally in line, although spaced farther than the one inch provided between sponges. The accumulated portion 26 of the linear connector is thus extended between the sponges by tensioning the connector. Where the connector is merely placed within the sponge, the accumulated portion provides very little resistance to extension. Alternatively, the resistance to extension may be controlled by providing a light adhesive bond between the accumulated portion and the sponge or by lightly stitching the accumulated portion. Similarly, the accumulated portion may be retained on the outside of the sponge, provided the accumulated portions of the retainer are lightly retained to the sponges.

As described, the first sponge may then be taken by the surgeon, letting out whatever length of connector is required to place the sponge at the operating site. The surgeon may obviously take two or more sponges and place them simultaneously, in which case the connector will be let out of two or more sponges. Where the connector is absorbent, as shown in FIGS. 1, 2 and 5, the connector provides additional absorbency for both the sponges and where placed. The connector should preferably be placed out of the operative field, such as along side the retractors, etc. used in conventional operating procedures. When it is desired to remove and dispose of the surgical sponges, as where the sponges become soaked with body fluids, the interconnected surgical sponges of this invention may be individually removed and disposed of. The sponge is simply removed from the operating site, tensioning the connector to permit discarding of one or more surgical sponges. Following this procedure, the surgeon then continues to use the surgical sponges, as required and disposing of the sponges when soaked or contaminated.

The interconnected surgical sponges of this invention thus substantially eliminate the danger of leaving a sponge in a patient, after closure. Even if a connector is cut during this procedure, the danger of leaving a sponge is minimal because the connector on either side of the cut sponge should indicate the presence of the sponge. Further, the connector may be brightly colored, such as blue or green, signifying the presence of a surgical sponge. The surgical sponges of this invention can thus substantially reduce the time consuming chore of counting the sponges before and after surgery and protect the patient from the possibility of leaving a sponge in the operating site. Further, all of the sponges utilized in an operation may now be easily identified, permitting weighing of the sponges, following surgery, to determine the loss of blood during an operation. It will be understood that various modifications may be made to the interconnected surgical sponges of this invention without departing from the perview of the claims, as described above.

I claim:

1. A plurality of serially interconnected surgical sponges for absorption of body fluids, comprising: a flexible linear element and at least two surgical sponges located along the length of said linear element, at least one of said sponges affixed to said element, the length of said linear element being greater than the composite length of said sponges and said element having a gathered portion greater in length than the length of a sponge, means releasably retaining substantially the entire gathered length of said linear portion to said sponge whereby said gathered portion is extensible between said sponges when tensioned for selectively and successively increasing the length between said sponges.

2. The interconnected sponges defined in claim 1, wherein said linear element is affixed to one end of each of said sponges and said gathered portion is disposed within each of said sponges for extension out of said sponges, between adjacent sponges, when tensioned.

3. The interconnected sponges defined in claim 2, wherein said element is an absorbent ribbon gathered within said sponges.

4. The interconnected sponges defined in claim 2, wherein said element is a flexible wire.

5. The interconnected sponges defined in claim 1, wherein said sponges include a tag indicator affixed to at least one of said sponges for identification of said sponge.

6. A plurality of absorbent surgical sponges and a linear retainer element interconnecting adjacent sponges, said sponges serially affixed along said element and said element having gathered portions received within each of said sponges, said retainer gathered portions having a length greater than the length of said sponges and extensible out of said sponges when tensioned to vary the distance between adjacent sponges, whereby said sponges may be selectively and successively spaced along said connector for use in absorbing body fluids.

7. The surgical sponges defined in claim 6, characterized in that said linear element is an absorbent ribbon lopped within said sponges and affixed adjacent one end of each of said surgical sponges and said sponges having an opening receiving said linear element through which said element is extended for varying the distance between adjacent sponges.

8. The surgical sponges defined in claim 7, characterized in that said ribbon is folded flat in a zig-zag pattern within said sponges in the plane of said surgical sponges.

9. The surgical sponges defined in claim 6, characterized in that said linear element is a wire lopped within said sponges and said sponges having an opening at one end receiving said wire and for extension of said wire therethrough, out of said sponges, to vary the length between adjacent sponges.

10. At least two absorbent surgical sponges and a linear connector, said connector having an accumulated portion greater in length than said sponges, said accumulated portion disposed within one of said sponges and fixed to opposed edges of said sponges and said connector extensible through an opening in said one sponge to increase the length between said sponges when said connector is tensioned, whereby the distance between said sponges may be varied by tensioning said connector.

11. The surgical sponges defined in claim 10, characterized in that said accumulated portion of said connector is at least 40 inches in length.

12. The surgical sponges defined in claim 10, wherein said connector is an absorbent ribbon folded within said one sponge.

13. The surgical sponges defined in claim 10, characterized in that said connector is a flexible wire looped within said one sponge.

14. The surgical sponges defined in claim 10, including at least four sterilized surgical sponges, each sponge having an accumulated connector portion disposed therein and packaged in face-to-face relation, said connector being continuous and serially interconnecting adjacent sponges.

* * * * *